United States Patent [19]

Williams, Jr.

[11] Patent Number: 4,573,482

[45] Date of Patent: Mar. 4, 1986

[54] ARTHROSCOPIC SURGERY METHOD

[75] Inventor: J. Webster Williams, Jr., Jacksonville, Fla.

[73] Assignee: Arthro-Medic, Inc., Jacksonville, Fla.

[21] Appl. No.: 600,444

[22] Filed: Apr. 16, 1984

Related U.S. Application Data

[63] Continuation of Ser. No. 394,709, Jul. 2, 1982, abandoned.

[51] Int. Cl.$^4$ .................................................. A61F 3/00
[52] U.S. Cl. ....................................................... 128/804
[58] Field of Search ................. 128/58, 804, 94, 99, 128/100, 133, 166, 474, 506–508, 518, 534, 567, 568, 584, DIG. 15, 4–8; 2/311–319; 24/3 A, 31 V; 36/71.5

[56] References Cited

U.S. PATENT DOCUMENTS

| | | | |
|---|---|---|---|
| 594,572 | 11/1897 | Slavik | 128/94 |
| 1,465,970 | 8/1923 | Cleveland et al. | 128/166 |
| 2,543,847 | 3/1951 | Hallstedt | 128/94 |
| 2,864,377 | 12/1958 | Montreys | 128/533 |
| 3,515,131 | 6/1970 | Stevens | 128/94 |
| 3,603,316 | 9/1971 | Lehman | 2/312 |
| 3,872,860 | 3/1975 | Noblitt | 128/DIG. 15 |
| 4,172,453 | 10/1979 | Leckie | 128/133 |
| 4,237,708 | 12/1980 | Bremer | 128/133 |
| 4,280,488 | 7/1981 | Polsky et al. | 128/804 |
| 4,289,122 | 9/1981 | Mason et al. | 128/804 |

FOREIGN PATENT DOCUMENTS

| | | | |
|---|---|---|---|
| 0602130 | 7/1978 | Chile | 2/311 |
| 911482 | 7/1946 | France | 2/312 |

Primary Examiner—Edward M. Coven
Assistant Examiner—Max F. Hindenburg
Attorney, Agent, or Firm—Arthur G. Yeager

[57] ABSTRACT

An arthroscopic surgery device comprising a flexible boot to fit snugly around a patient's ankle and adjacent portions of the foot and leg and a belt to be worn around the waist of the surgeon; the boot having on the outside surface of the rear portion an area of fabric loops, the belt having a lateral band portion extending upwardly and downwardly from the waistband portion with the surface of the lateral band facing away from the surgeon being substantially covered with fabric hooks and the surface of the lateral portion facing toward the surgeon being covered with fabric loops, the length of the lateral band portion being sufficient to wrap around in overlapping relationship the boot encasing the foot of a patient. This device is employed to hold and to position the patient's leg primarily the knee, in any desired orientation to permit surgery thereon.

5 Claims, 6 Drawing Figures

ARTHROSCOPIC SURGERY METHOD

This is a continuation of application Ser. No. 394,709 filed July 2, 1982, now abandoned.

BACKGROUND OF THE INVENTION

Arthroscopic surgery includes surgery on the knee which requires that the lower leg be twisted to any desired position while the knee is unbent or bent in any angle so as to provide the best positioning for the surgery that is required. Previously, it had been necessary to provide an assistant to hold the foot and ankle or adjacent portions of the leg and twist the leg and bend the knee to any of an infinite number of positions and to hold the desired positions steady so that the delicate surgery can be preformed by the surgeon. It is an object of the present invention to provide a simple apparatus which permits the surgeon to manipulate the patient's leg to any desired position for the surgery and to move it at any time to permit the optimun in the surgical procedure. It is another object of this invention to provide a simple apparatus employing flexible fabric with the capability of holding the patient's leg in a steady position without discomfort to the patient. It is also an object of this invention to provide a means for the surgeon to make minor adjustments in the positioning of the patient's knee whenever required during the surgical operation and to accomplish this by himself without the need for an assistant and the time consuming adjustments by others. Still other objects will be apparent from the more detailed description of this invention which follows.

BRIEF DESCRIPTION OF THIS INVENTION

This invention provides a leg holding apparatus for use in arthroscopic surgery including a patient's boot and a surgeon's belt. The boot is snugly fastened around the instep, heel, ankle, and lower leg of the patient and has on its rear outer surface one portion of a releasable fastener extending from the part adjacent the heel to the part adjacent the lower leg. The belt includes a waistband adapted to fit nugly around surgeon's waist and a lateral connecting band portion extending generally upwardly and downwardly from the waistband and positioned adjacent the location where the surgeon's arm in its normal hanging position crosses the waistband. The connecting band portion has the cooperating portion of the releasable fastener so that it may be detachably secured to the portion of a releasable fastener on the boot. In its preferred embodiment a second lateral connecting band portion is spacedly positioned on the belt so that the ankle of either foot may be attached to the belt on either side of the surgeon.

In one specific embodiment the releasable fastener portions are the two cooperating features of a VELCRO fastener; namely a fabric loop portion and a fabric hook portion. In another embodiment the connecting band portions are straps attached at their midjoints to the waist band and are capable of wrapping tightly around the boot in overlapping relationship.

BRIEF DESCRIPTION OF THE DRAWINGS

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

DETAILED DESCRIPTION OF THE INVENTION

Figure 1:
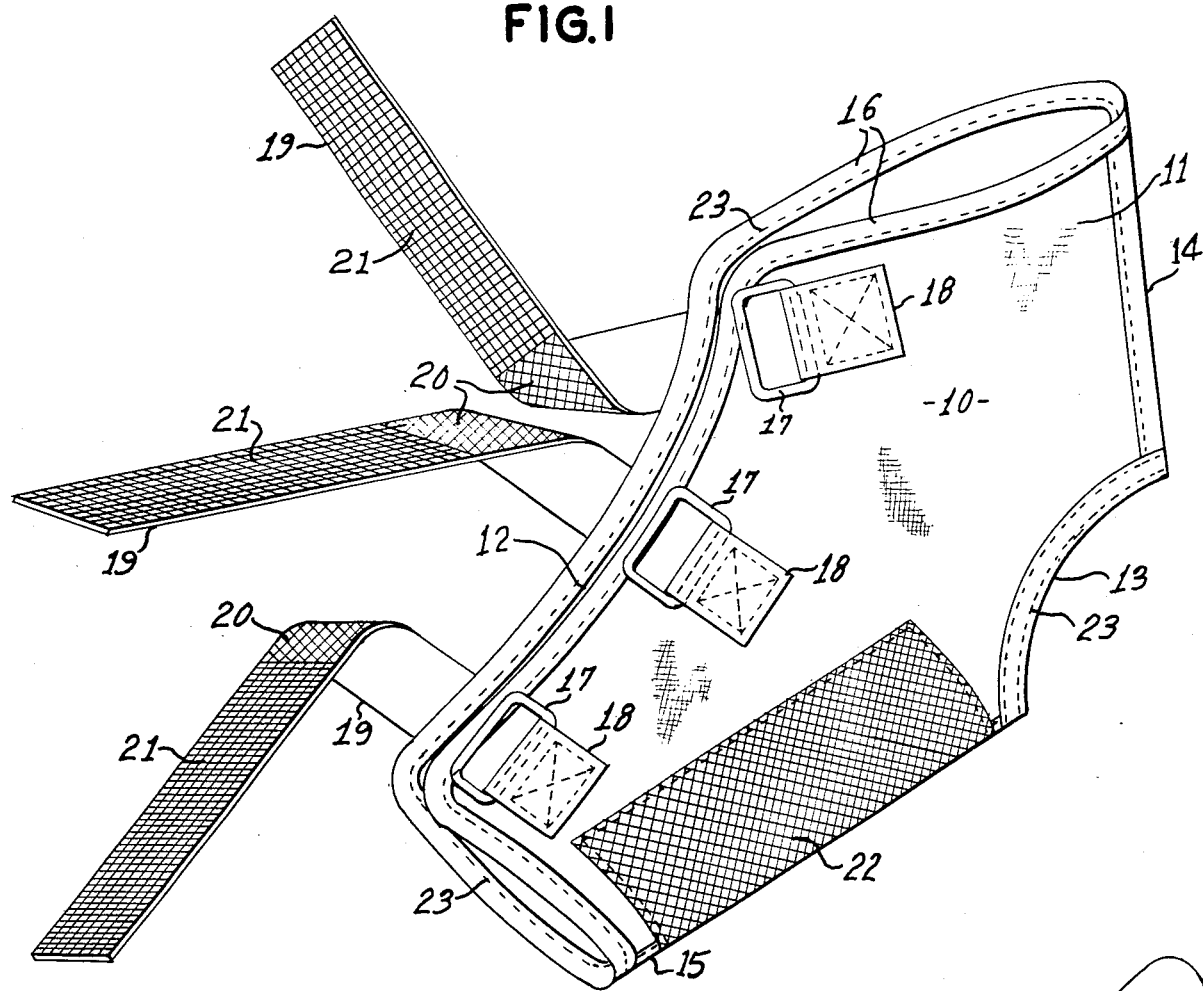
FIG. 1 is a schematic illustration in perspective of the boot of this invention.
Figure 2:
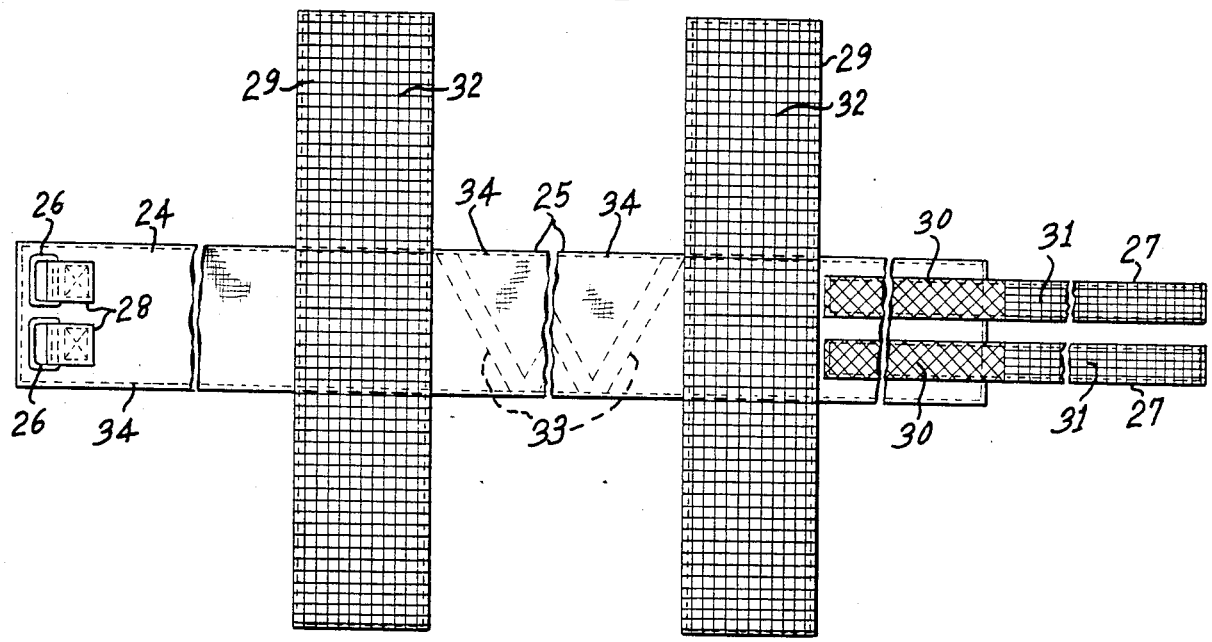
FIG. 2 is a top plan view of the outside of the belt of this invention.
Figure 3:
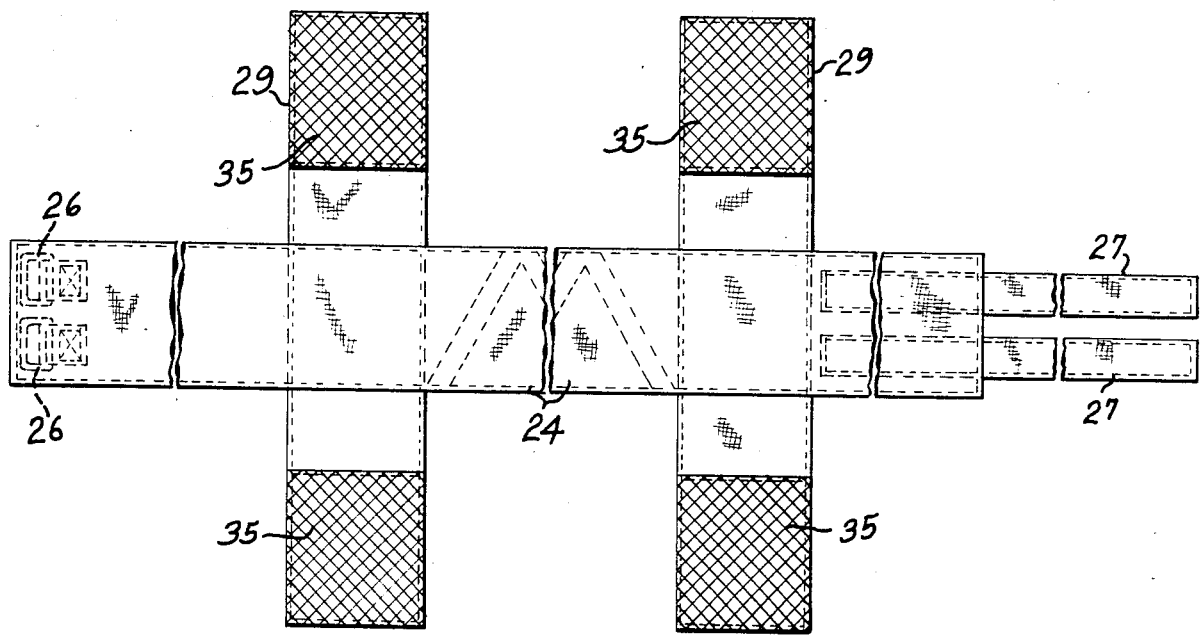
FIG. 3 is a bottom plan view of the inside of the belt of this invention.

The apparatus of this invention includes the cooperating action of a boot, as shown in FIG. 1, and a belt, as shown in FIGS. 2 and 3. Boot 10 is a simple wrap-around structure which is fastened snugly in place by any suitable means so as to fit around the ankle and heel portion of a patient's leg from about the instep to the lower portion of the leg immediately above the ankle. Preferably boot 10 is made of a flexible fabric, e.g. heavy canvas, that can be fashioned to fit this portion of the leg. In FIG. 1 it may be seen that the boot has two side panels 11 which are stitched together along the back and bottom to provide a boot having a front opening 12, a heel opening 13 and portions joined together by stitching along a foot tape 14 and a leg tape 15. In order to finish the edges in a smooth fashion edging tape 16 is stitched at 23 along any raw cut edges. Boot 10 may be closed snugly about the foot of the patient by any appropriate, releasable means including a plurality of spaced D-ring buckles 17 secured by fabric ring holder 18 sewed to one side panel 11 and corresponding spaced buckling tapes 19 sewed to the other side panel 11. Appropriate portions of tape 19 are covered with fabric loops 20 and with fabric hooks 19 so that tapes 19 may be inserted through D-rings 17, bent back on themselves and secured firmly by the cooperative action of the fabric hooks and the fabric loops forming a releasable fastener means, commonly called a VELCRO fastener.

In FIGS. 2 and 3 the structure of the belt of this invention is depicted in which belt 24 includes a waistband 25 that is fastenable around the waist of the surgeon by the cooperating action of D-rings 26 and buckling tapes 27. D-rings 26 are secured in place on the outside of the belt by fabric ring holding members 28 sewn onto belt 24. Buckling tapes 27, also sewn on the outside of belt 24, contain on their outside surfaces a portion of fabric hooks 31 and a portion of fabric loops 30 so that tapes 27 may be inserted into D-rings 26 and folded back upon themselves to engage fabric hook section 31 with fabric loop section 30 to provide a non-slip fastening to accommodate the belt securely to different waist sizes of different surgeons.

Lateral connecting band portions 29 are spacedly attached firmly, as by sewing, waistband 25 and positioned such that, when belt 24 is around the waist of the surgeon, lateral connecting band portions 29 will be respectively on the two sides of the surgeon, generally in the location where the arm in its normal hanging position crosses belt 24. Lateral connecting band portions 29 contain on the outside surface, i.e. the surface facing away from the surgeon, fabric hooks 32 and on the inside surface, i.e. the surface facing toward the surgeon, fabric loops 35. The total length of each band portion 29 is such that it may be wrapped around the boot encasing the ankle portion of the patient and will allow sufficient overlapping of the two ends of lateral connecting band portion 29 to permit hooks 32 to engage loops 35 in a firm engagement. The width of waistband portion 25, and the width of lateral connecting band portions 29 may each be about four inches with band portions 29 extending about six to seven inches beyond each edge of belt 24, making the entire length of each lateral connecting band portion 29 about sixteen to eighteen inches. In order to prevent wasitband 25 from curling or becoming distorted it is preferable that stiffening stays 33 be inserted internally in the structure of the waistband between the two lateral connecting band portions 29. It is preferred that belt 24 be made of a fabric material that can be readily and easily sterilized, and be sufficiently strong to be repeatedly used. Accordingly, a heavy canvas is suitable in that it may be fashioned into the proper shape by stitching 34 at appropriate locations.

Figure 4:
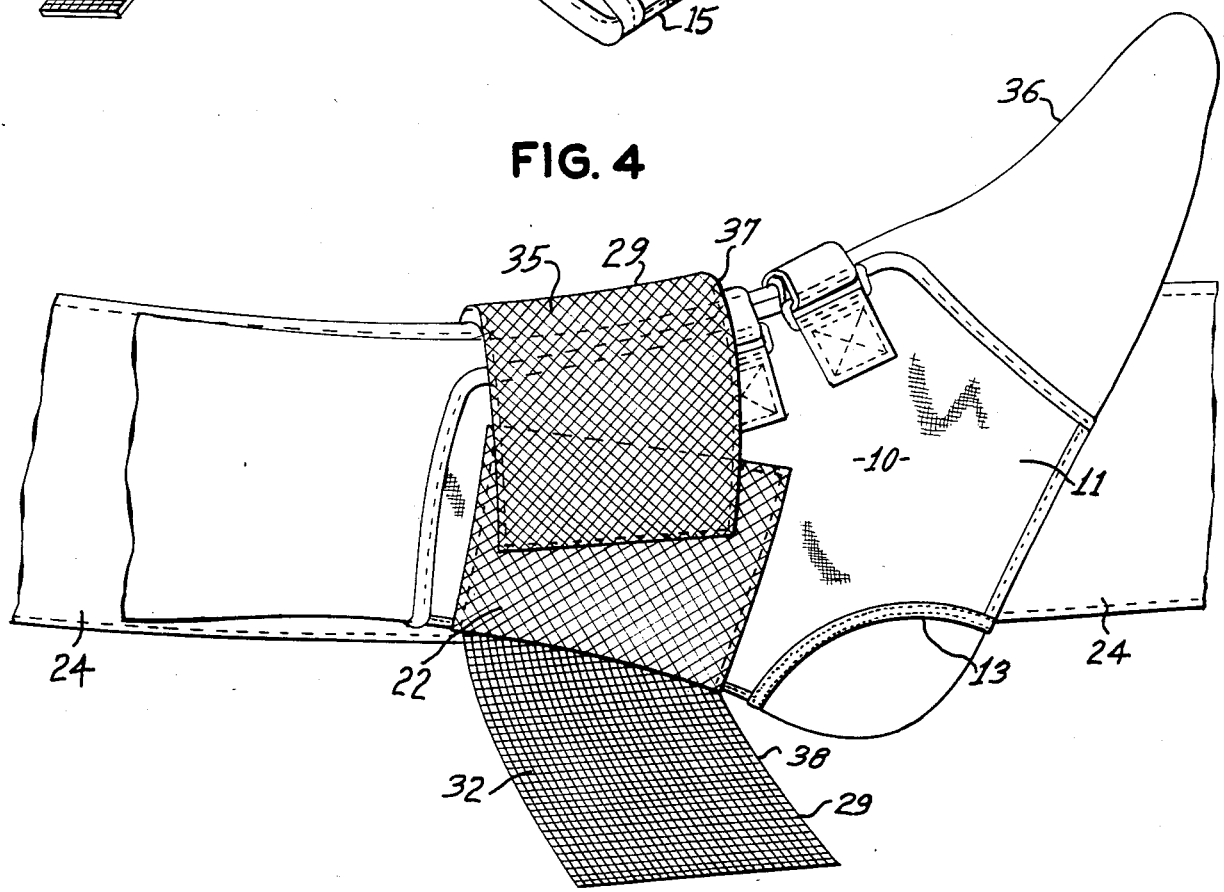
FIG. 4 is a schematic illustration of the boot of this invention applied to a patient's foot and in the process of being attached to the belt of this invention.

In FIG. 4 the foot of a patient is being wrapped and positioned onto belt 24 which is around the waist of the surgeon. Boot 10 is buckled around the foot 36 of the patient leaving surface area 22 of fabric loops on the outside of the foot. When the foot with the boot attached is laid against belt 24 with lateral connecting band portions 29 open the top portion thereof may be wrapped around the top of the leg such that its fabric hook section will attach itself firmly to the fabric loop section 22 on boot 10. The lower portion of lateral connecting band 29 may then be wrapped around and overlapping over upper portion of lateral band 29 with fabric hook portions 32 making firm and nonslip engagement with fabric loops 22 of the boot and fabric loops 35 on band 29. This permits the foot 36 of the patient to be snugly attached to belt 24 through engagement of loop portion 22 of the boot with 32 of connecting band 29.

Figure 5:
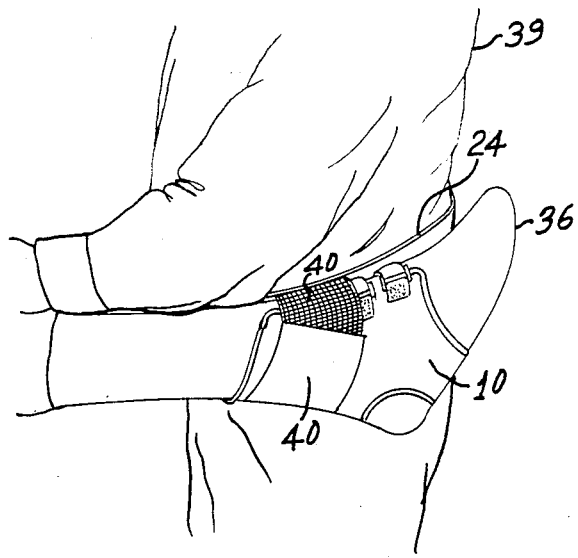
FIG. 5 is a schematic illustration of a surgeon with the belt around his waist and the leg of a patient encased in the boot and attached to the belt in accord with this invention.
Figure 6:
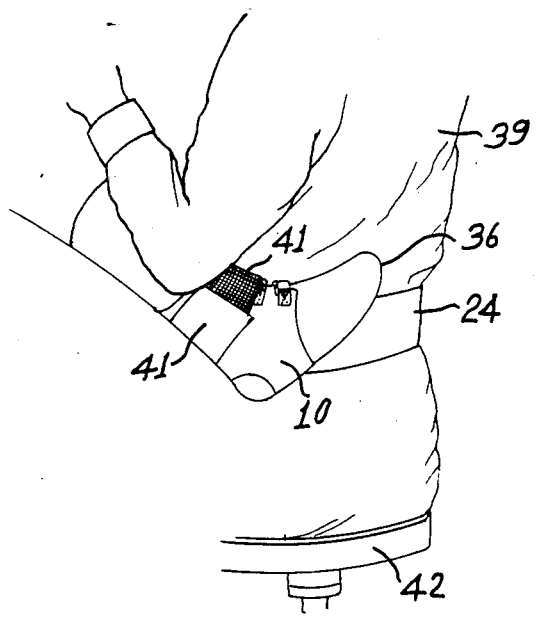
FIG. 6 is an embodiment similar to that of FIG. 5 except that the surgeon has placed the leg in flexion by sitting on a stool.

In FIG. 5 it may be seen how the lateral band portions 40 appear after being overlapped around the foot of patient 36 encased in boot 10. Surgeon 39 in this position has the patient's leg attached to his waist belt 24 and he can move in any direction to position the leg exactly as he wishes it to be. For example if the surgeon wishes the leg to be in extension he may move away from the patient with the result as shown in FIG. 5. On the other hand if the surgeon wishes the leg to be flexion, he may move closer to the patient and reposition boot 10 at a slightly different angle to belt 24 and even may be seated on a stool 42 as shown in FIG. 6. As the surgeon proceeds with the operation it may become desirable to extend the leg, flex the knee, or twist the lower leg to provide better access to the area being examined, and it is only necessary for the surgeon to move slightly from one position to another, raise or lower stool 42 or do any of several other small movements which permit the surgeon to adjust the leg to exactly to where he wants it to be without repositioning and reattaching the boot to the belt.

Belt 24 as seen in FIGS. 2 and 3 has two spaced lateral connecting band portions 29 but it should be clear that for many procedures a single band portion 29 is all that is required. Also a single lateral connecting band portion 29 may be provided with a detachable VELCRO type connection between portion 29 and belt 24, if desired, with the belt 24 having two releasable portions affixed thereto beneath the arm positions of a surgeon so that the single band portion 29 may be affixed to either one. It is also obvious that the positioning of band portions 29 need not be such that band portions 29 fall directly under the arms of the surgeon, but may be positioned sightly fore or aft thereof.

The fabric loops and fabric hooks as employed herein are well known and are available in one embodiment commercially under the trademark VELCRO of Scovill Manufacturing Company Cleveland, Ohio.

While the invention has been described with respect to certain specific embodiments, it will be appreciated that many modifications and changes may be made by those skilled in the art without departing from the spirit of the invention. It is intended, therefore, by the appended claims to cover all such modifications and changes as fall within the true spirit and scope of the invention.

What is claimed as new and what is desired to secure by Letters Patent of the United States is:

1. In a process in which a surgeon performs arthroscopic surgery on the knee of a patient the improvement which comprises placing around the foot of said patient a boot having means for releasably applying and snugly fastening said boot around the foot and lower leg of the patient whereby rotative movement of said boot will cause twisting of the leg and knee, said boot having a releasable fastener portion on its outside surface, placing around the waist of said surgeon a belt having a waistband with releasable fastening means at the two ends thereof to provide an adjustable snug fit around the surgeon's waist and having connecting means extending laterally of said belt and positioned generally midway between an end of the belt and a point halfway between said two ends, which include a releasable fastener portion adapted to releasably engage said fastener portion on said boot placing the patient's foot encased in said boot in a selected orientation against said belt adjacent one of said connecting means, wrapping said connecting means around said boot to engage said releasable fastener portions thereof whereby movement of said surgeons waist produces flexure or twisting of said knee.

2. The process of claim 1 wherein said connecting means includes an elongated band extending upwardly and downwardly from said belt.

3. The process of claim 1 in which one of said releasable fastener portions is a fabric hook portion and the other cooperating releasable fastener portion is a fabric loop portion.

4. The process of claim 3 in which said one fastener portion is on said connecting means and said other fastener portion is on said boot.

5. The process of claim 4 wherein the surface of said connecting means is substantially covered with fabric hooks on one side thereof and substantially covered with fabric loops on the other side thereof, and the outside of said boot is covered with fabric hooks or fabric loops to engage with the surface of said connecting means that is in contact with the outside of said boot.

* * * * *